(12) United States Patent
Kramer

(10) Patent No.: US 9,763,781 B2
(45) Date of Patent: Sep. 19, 2017

(54) INFLATABLE TRANSCATHETER INTRACARDIAC DEVICES AND METHODS FOR TREATING INCOMPETENT ATRIOVENTRICULAR VALVES

(71) Applicant: George Kramer, Westbury, NY (US)

(72) Inventor: George Kramer, Westbury, NY (US)

( * ) Notice: Subject to any disclaimer, the term of this patent is extended or adjusted under 35 U.S.C. 154(b) by 522 days.

(21) Appl. No.: 14/272,145

(22) Filed: May 7, 2014

(65) Prior Publication Data
US 2014/0336751 A1 Nov. 13, 2014

Related U.S. Application Data

(60) Provisional application No. 61/820,601, filed on May 7, 2013.

(51) Int. Cl.
*A61F 2/24* (2006.01)
(52) U.S. Cl.
CPC .......... *A61F 2/2433* (2013.01); *A61F 2/246* (2013.01); *A61F 2/2457* (2013.01); *A61F 2250/0003* (2013.01)
(58) Field of Classification Search
CPC .................. A61F 2/2433; A61F 2/246; A61F 2250/0003; A61F 2/2457; A61M 2025/1084
USPC ....................................................... 623/2.11
See application file for complete search history.

(56) References Cited

U.S. PATENT DOCUMENTS

| | | | |
|---|---|---|---|
| 3,451,067 A | | 6/1969 | Jordan |
| 4,998,539 A | * | 3/1991 | Delsanti ............. A61F 2/90 128/898 |
| 5,336,178 A | * | 8/1994 | Kaplan ............... A61B 8/12 604/103.01 |
| 5,556,382 A | * | 9/1996 | Adams ............. A61M 25/104 604/103.09 |
| 5,795,325 A | * | 8/1998 | Valley ........... A61B 17/12022 604/103.1 |
| 6,090,097 A | * | 7/2000 | Barbut .......... A61B 17/12022 604/506 |
| 6,245,040 B1 | * | 6/2001 | Inderbitzen ....... A61M 25/104 604/103.07 |
| 6,471,672 B1 | * | 10/2002 | Brown ............... A61F 2/958 604/101.01 |
| 6,500,186 B2 | * | 12/2002 | Lafontaine ....... A61B 17/3207 606/159 |
| 7,691,119 B2 | * | 4/2010 | Farnan ................ A61F 2/86 606/159 |
| 7,731,693 B2 | * | 6/2010 | Melsheimer ........ A61M 25/09 600/585 |
| 7,837,727 B2 | | 11/2010 | Goetz et al. |

(Continued)

*Primary Examiner* — Amy R Weisberg
(74) *Attorney, Agent, or Firm* — Daniel P. Burke & Associates, PLLC

(57) ABSTRACT

Inflatable heart valve implants and methods utilizing those valves designed to reduce or eliminate the regurgitant jet associated with an incompetent atrioventricular valve. The heart valve implants, which are deployed via a transcatheter venous approach, comprise an inflatable balloon portion movably connected to an anchored guide shaft and movable from a distal position in the ventricle to a more proximal position between leaflets of a native atrioventricular valve. The range of movement of the inflatable valve body can be adjusted in situ after or before the guide shaft has been anchored to native heart tissue during surgery.

24 Claims, 11 Drawing Sheets

(56) References Cited

U.S. PATENT DOCUMENTS

| | | | |
|---|---|---|---|
| 8,025,636 B2* | 9/2011 | Eidenschink | A61M 25/10 604/96.01 |
| 8,092,525 B2 | 1/2012 | Eliasen et al. | |
| 8,182,507 B2* | 5/2012 | Anderson | A61B 17/221 606/200 |
| 8,449,606 B2 | 5/2013 | Eliasen et al. | |
| 2001/0007931 A1* | 7/2001 | Blatter | A61M 25/10 604/103.01 |
| 2004/0249408 A1* | 12/2004 | Murphy | A61F 2/2487 606/198 |
| 2007/0027520 A1* | 2/2007 | Sherburne | A61F 2/958 623/1.11 |
| 2007/0093890 A1* | 4/2007 | Eliasen | A61F 2/246 623/2.11 |
| 2007/0255399 A1* | 11/2007 | Eliasen | A61F 2/246 623/2.36 |
| 2007/0265700 A1* | 11/2007 | Eliasen | A61F 2/246 623/2.1 |
| 2007/0293943 A1* | 12/2007 | Quinn | A61F 2/246 623/2.11 |
| 2008/0249464 A1* | 10/2008 | Spencer | A61M 25/1002 604/103 |
| 2008/0288061 A1* | 11/2008 | Maurer | A61F 2/246 623/2.36 |
| 2010/0036410 A1* | 2/2010 | Krolik | A61B 17/22032 606/194 |
| 2010/0152717 A1* | 6/2010 | Keeler | A61B 18/24 606/7 |
| 2010/0179649 A1 | 7/2010 | Richter et al. | |
| 2011/0022164 A1* | 1/2011 | Quinn | A61F 2/246 623/2.11 |
| 2011/0077733 A1 | 3/2011 | Solem | |
| 2012/0179244 A1 | 7/2012 | Schankereli et al. | |
| 2013/0190798 A1* | 7/2013 | Kapadia | A61F 2/246 606/195 |
| 2014/0142505 A1* | 5/2014 | Lin | A61M 25/1029 604/103.06 |
| 2015/0250991 A1* | 9/2015 | Silvestro | A61M 29/02 606/194 |

* cited by examiner

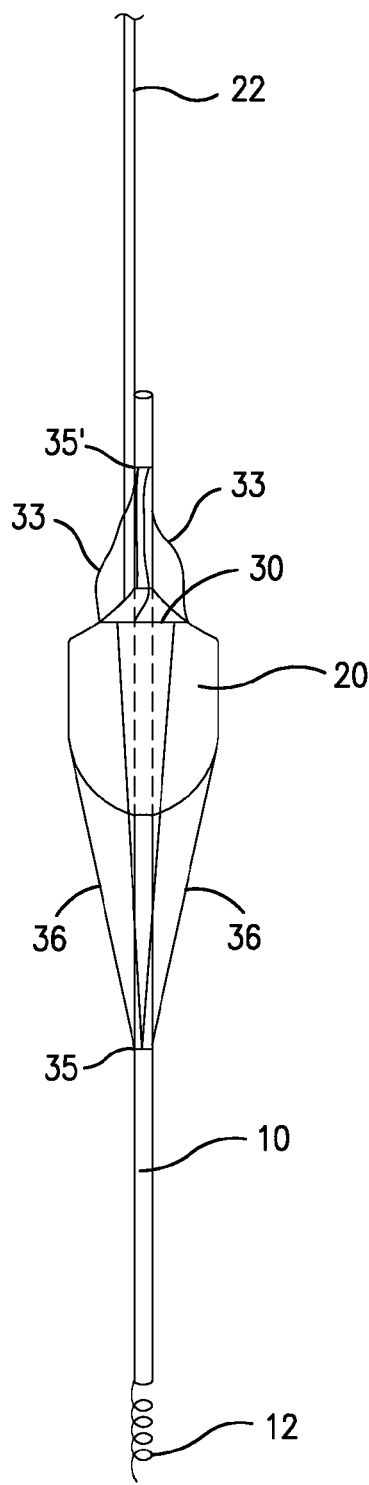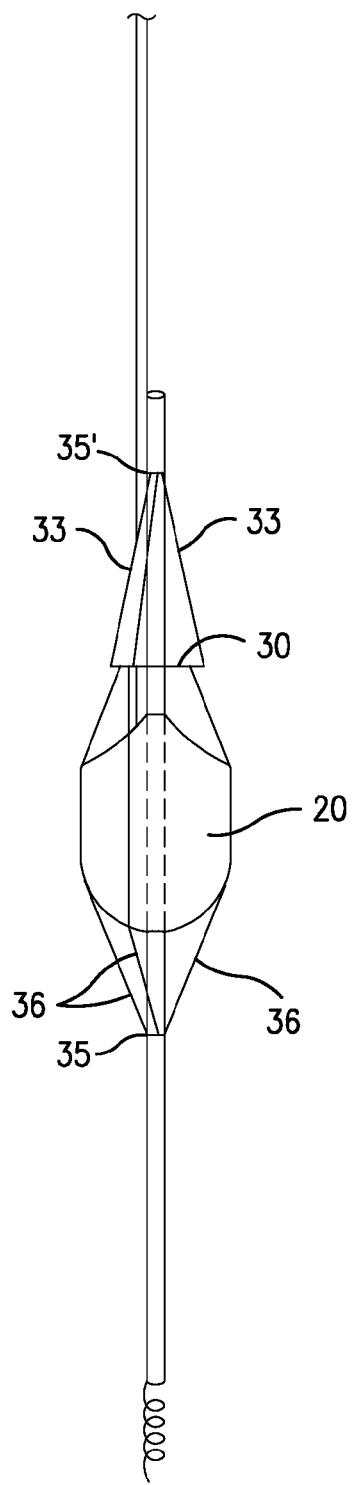
FIG. 2  FIG. 3

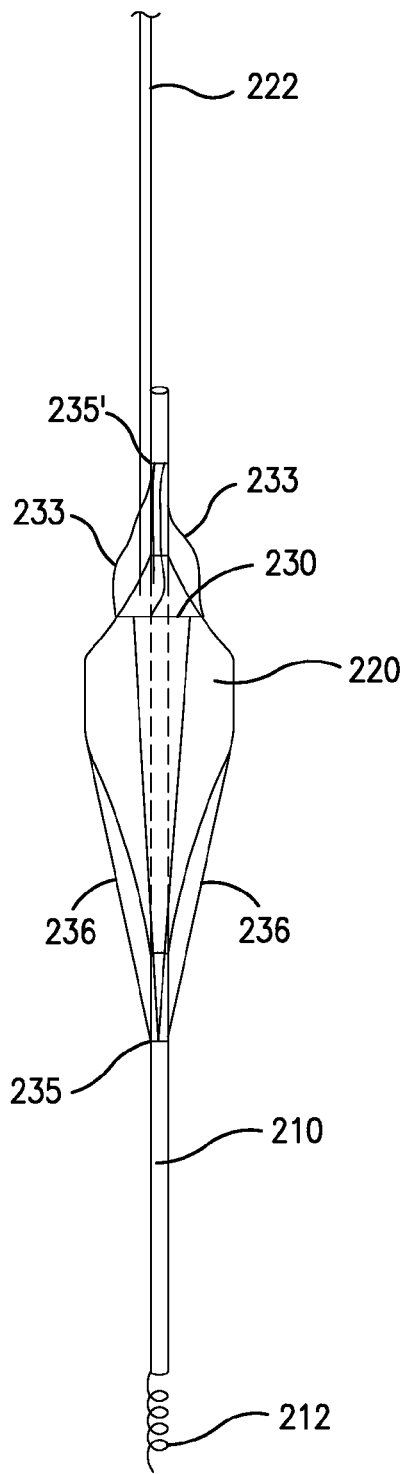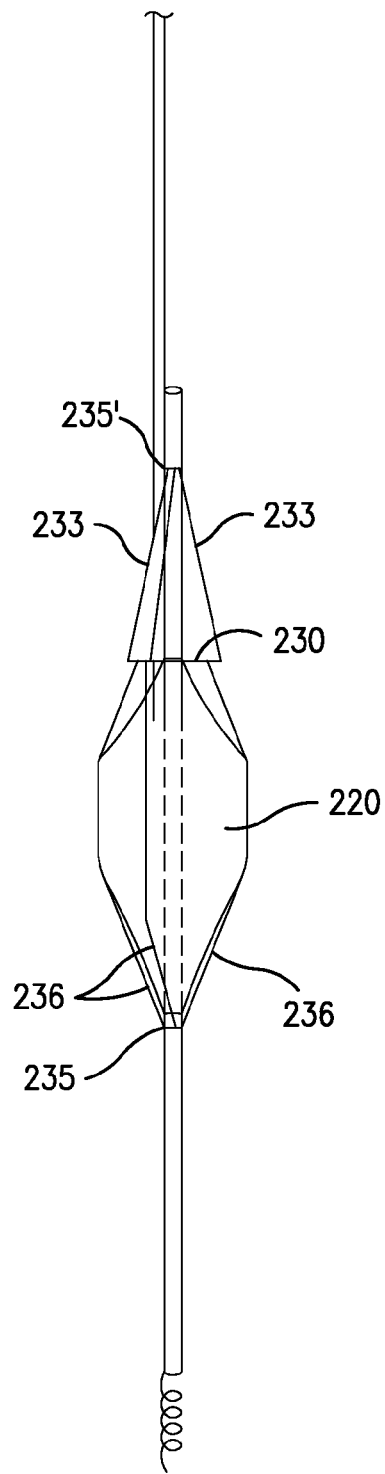
FIG. 10  FIG. 11

INFLATABLE TRANSCATHETER INTRACARDIAC DEVICES AND METHODS FOR TREATING INCOMPETENT ATRIOVENTRICULAR VALVES

RELATED APPLICATION

This application claims priority on U.S. provisional patent application Ser. No. 61/820,601 filed May 7, 2013.

The present invention is directed to inflatable heart valve implants and methods utilizing those valves designed to reduce or eliminate the regurgitant jet associated with an incompetent atrioventricular valve. The embodiments comprise devices and methods wherein, via a transcatheter venous approach, an inflatable balloon portion is movably disposed along an anchored guide shaft from a distal position in the ventricle to a more proximal position between leaflets of a native atrioventricular valve.

BACKGROUND

Some previously known methods of treating incompetent, i.e. leaking, atrioventricular valves comprise the steps of removing the patient's native valve leaflets and replacing them with an artificial valve. Some artificial valves, particularly those which are designed to be substantially stationery or fixed relative to the valve annulus, can create a substantial risk of stenosis or obstruction to the desired flow of blood into the ventricle.

SUMMARY

The various embodiments of the present invention comprise methods and devices for treating an incompetent atrioventricular heart valve without removing the existing valve leaflets and in a manner which does not create a substantial obstruction to the inflow of blood through the valve during the diastolic portion of the cardiac cycle.

The valve devices are inflatable transcatheter intracardiac devices designed for placement within an incompetent native atrioventricular valve apparatus (i.e. mitral or tricuspid). As used herein, the term "native" is meant to indicate that the original leaflets of the atrioventricular valve have not been removed. The disclosed valve devices reduce or eliminate the regurgitant jet associated with the incompetent valve with an inflatable balloon which is movably positioned relative to, and preferably on, a guide shaft anchored to the heart wall. The inflated balloon portion occupies the regurgitant valve orifice and coapts with the native leaflets to create a better seal during the systolic portion of the cardiac cycle. The inflated balloon portion is then moved distally into the ventricle by the inflow of blood during the diastolic portion of the cardiac cycle to minimize the obstruction of blood flowing into the ventricle. Some embodiments comprise adjustable attachments between the guide shaft and range limiting structures which limit the range of proximal and distal movement of the balloon portion relative to the guide shaft and discernible indicia to assist the surgeon with proper placement of the valve device during surgery. Thus, while the heart valve implant is initially provided such that the balloon has some predetermined range of movement relative to the guide shaft, that range of movement can be changed, i.e. adjusted. As used herein, the term "predetermined" is not used to indicate that a given range of movement is permanent.

The methods comprise the steps of anchoring one of the valve devices to a heart wall and inflating the movable balloon portion. Some methods also comprise the steps of radiographically observing the range of motion of the inflated balloon on the guide shaft via fluoroscopy and transesophageal echocardiography and adjusting the positioning of at least one of the range limiting structures which limit the extent of movement of the balloon in order to properly position the inflated balloon for optimal sealing and blood flow. As used herein, the terms "balloon" and "inflatable valve body" are used interchangeably.

BRIEF DESCRIPTION OF THE DRAWINGS

FIG. 2 illustrates a first valve device of the present invention with the balloon inflated and in the proximal position.

FIG. 3 illustrates a valve device of FIG. 1 with the balloon inflated and in the distal position.

FIG. 10 illustrates the valve device of FIG. 9 with the balloon inflated and in the proximal position.

FIG. 11 illustrates a valve device of FIG. 9 with the balloon inflated and in the distal position.

DETAILED DESCRIPTION

Figure 1:
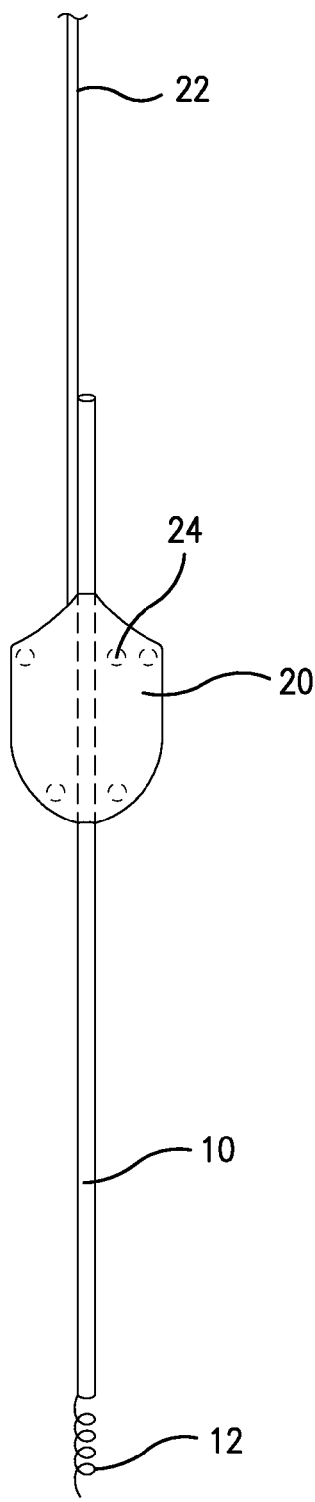
FIG. 1 is a partial view of a first valve device of the present invention.

One valve device of the present invention comprises a flexible shaft which may have an outer layer of polyurethane or a silicon rubber coating with an active fixation distal end. With reference to FIG. 1 which is a partial view of a first embodiment with elements removed for clarity, a guide shaft 10 comprises an anchor 12 at its distal end. Anchor 12 is generally in the form of a spiral screw and is adapted to be secured to a heart wall by rotating the internal portion of the shaft during transcatheter placement. Anchor 12 can be integrally formed with shaft 10 or separately formed and connected proximate the distal end of shaft 10. An inflatable balloon 20 is movably positioned relative to shaft 10 within a range of motion described below. Balloon 20 is preferably mounted on shaft 10. The balloon is also preferably tapered on both ends to promote laminar blood flow around the balloon thereby decreasing the likelihood of thrombogenesis.

An inflation lumen 22 is used for inflating and deflating the balloon. The inflation lumen extends to a point outside the surgical site for access by the surgeon. In one embodiment, the inflation lumen is detachable from the balloon after inflation. In this embodiment, the device is then self-contained within the heart. This decreases the risk of thrombosis. In another embodiment, the inflation lumen is not detachable thereby facilitating deflation of the balloon for subsequent removal.

All components are formed of suitable materials. Balloon 20 is preferably formed of ePTFE but can be formed of other materials known in the art, such as polypropylene. Balloon 20 also preferably comprises markers 24, e.g. metal tags, (illustrated in dashed lines in the figures) implanted in distal and proximal portions of the balloon to permit a surgeon to observe the balloon's position and range of motion via fluoroscopy.

The range of motion of balloon 20 along shaft 10 is limited in both the proximal and distal directions by range limiting structure. With reference to FIGS. 2 and 3, this embodiment comprises a ring 30, sometimes referred to herein as a pseudo-annulus ring 30. The internal opening of the ring 30 is smaller than the outer diameter of the inflated balloon 20 so that the inflated balloon 20 cannot pass through ring 30. Ring 30 is connected to a proximal portion of the shaft 10 by a plurality of proximal artificial chordae tendineae 33. The ring 30 is also connected to a more distal portion of the shaft 10 by a plurality of distal artificial chordae tendineae 36. In preferred embodiments, the distal artificial chordae tendineae 36 are connected to shaft 10 at a position which is spaced from the distal end of shaft 10. Preferably, when measured from the location where the proximal artificial chordae tendineae are connected to the shaft 10, the distal artificial chordae tendineae are connected to the shaft at a location spaced by a distance of less than 80% of the distance between the connection of the proximal artificial chordae tendineae to the shaft 10 and the distal end of shaft 10, more preferably less than 50% of this distance, and most preferably about one-third of this distance. Movement of the balloon is preferably restricted to the proximal third of the ventricle after the valve device has been implanted. By avoiding excessive motion of the balloon, the risk of trauma to the heart wall by the moving balloon is minimized. In this embodiment, all of the artificial chordae tendineae are secured to shaft 10. The ring 30 is preferably positioned slightly proximally of the atrioventricular annulus.

As shown in FIG. 2, the proximal movement of the balloon 20 is limited by the length of the distal artificial chordae tendineae which extend from the shaft 10, pass around the balloon 20, and then to ring 30. Balloon 20 is moved to this proximal position illustrated in FIG. 2 during the systolic portion of the cardiac cycle. In this configuration, the proximal artificial chordae tendineae 33 are unloaded, i.e. not under load, or slack as shown in FIG. 2.

As shown in FIG. 3, the distal range of motion of balloon 20 is constrained by the distal artificial chordae tendineae 36 which are attached at their proximal ends to the ring 30 whose distal movement is constrained by the length of the proximal artificial chordae tendineae 33. As balloon 20 moves distally at the beginning of the diastolic portion of the cardiac cycle, the proximal artificial chordae tendineae 33 become taut, thereby limiting the distal movement of ring 30. The balloon 20 will move distally until the tautness of the distal artificial chordae tendineae 36 arrests the further distal movement of the balloon 20. The artificial chordae tendineae 33, 36 of this embodiment and the pseudo-annulus ring 30 are also preferably formed of flexible ePTFE suture material, or other biocompatible filaments commonly used for sutures within the heart and blood vessels. The inherent properties of the artificial chordae tendineae and the pseudo-annulus ring provide for the progressive deceleration of the balloon which provides for the gradual closure of the valve which mimics the normal motion of a healthy, native valve apparatus during the cardiac cycle.

Figure 4:
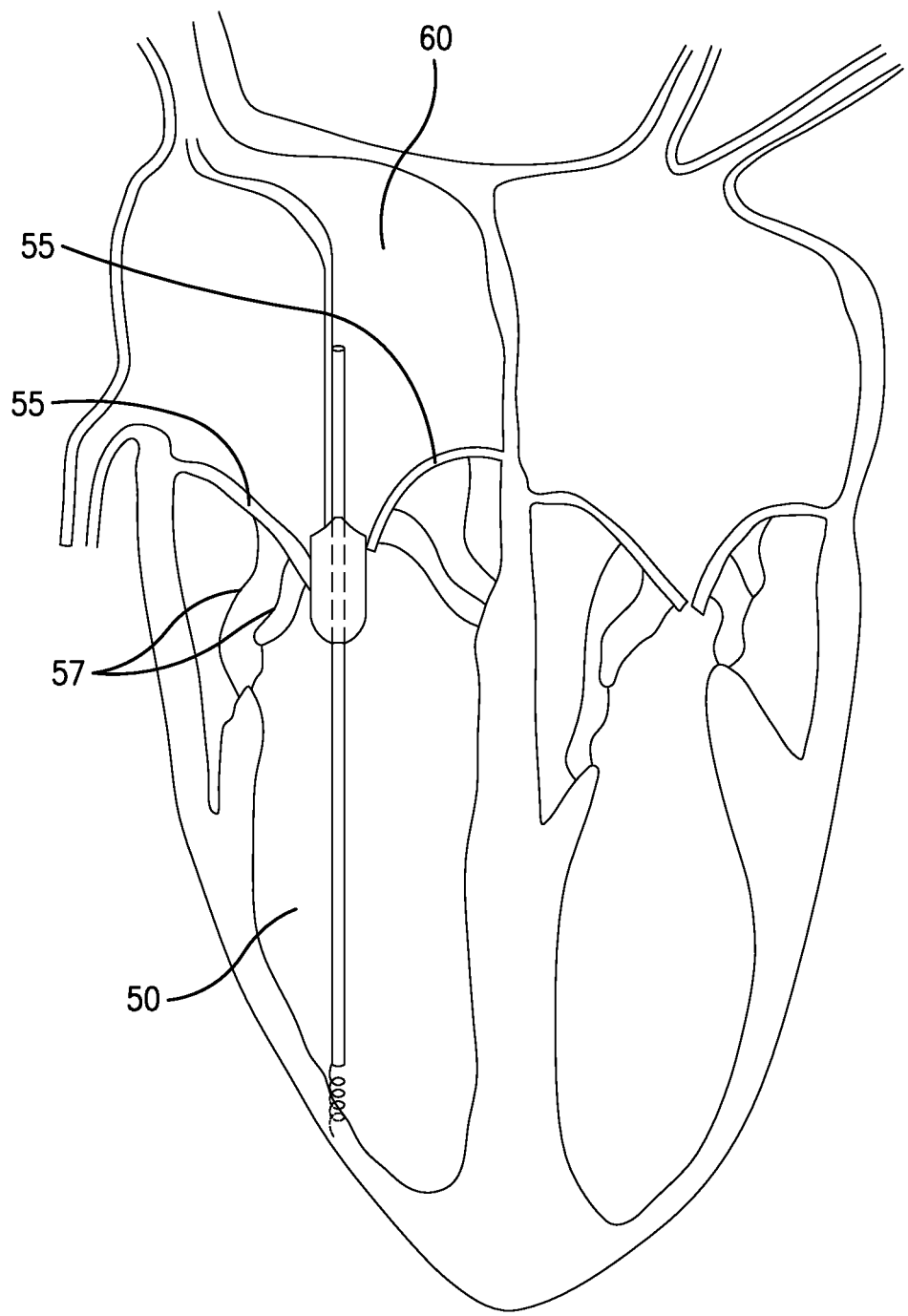
FIG. 4 is a view of a valve device of FIG. 1 shown in a heart during the systolic portion of the heart cycle.
Figure 5:
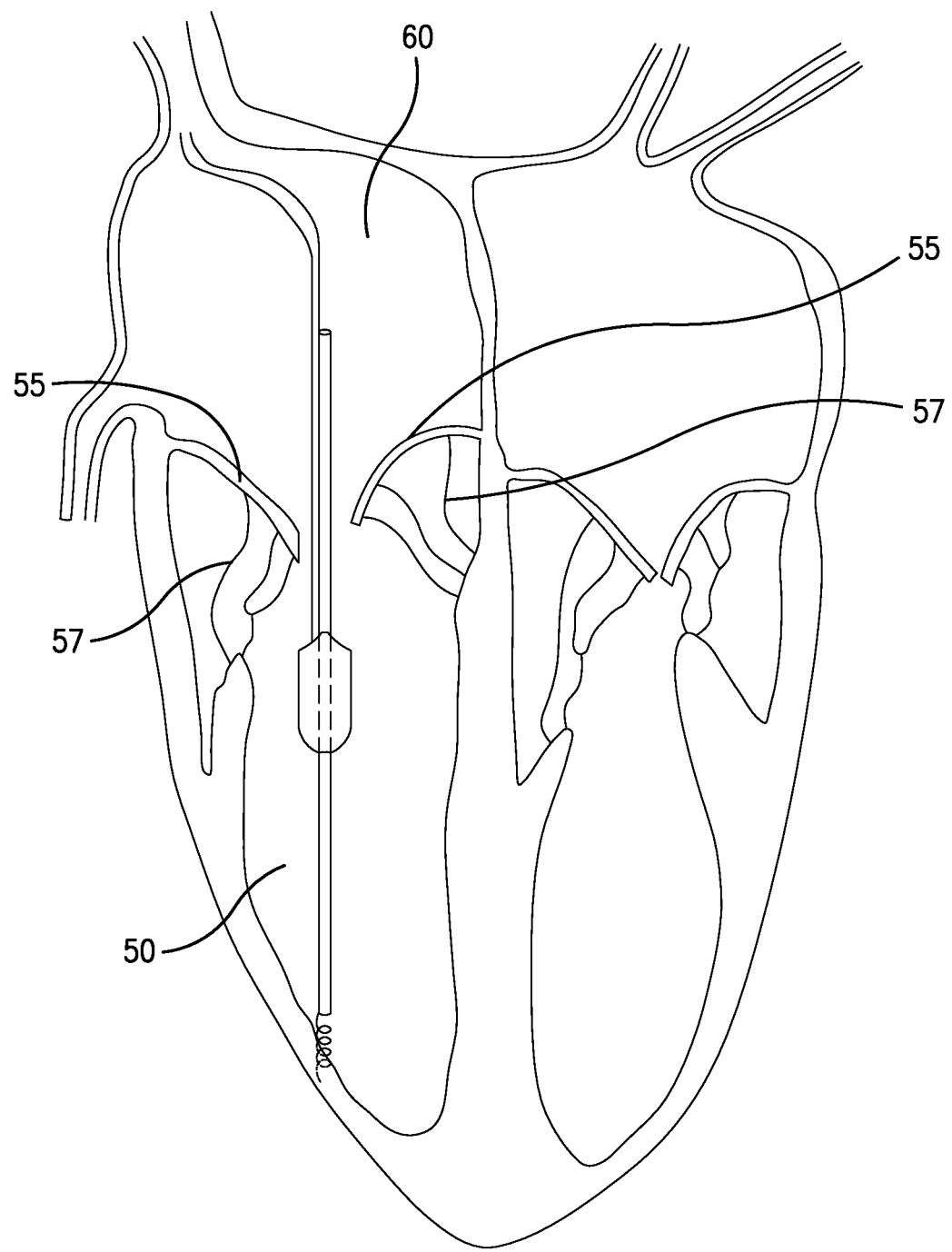
FIG. 5 is a view of a valve device of FIG. 1 shown in a heart during the diastolic portion of the heart cycle.

FIGS. 4 and 5 illustrate the embodiment shown in FIGS. 1-3 installed in a right ventricle 50 with the balloon 20 inflated. FIGS. 4 and 5 are not meant to be exact representations of an actual heart, but suffice to illustrate the positioning of the valve device relative to the leaflets 55 whose proximal movement are normally limited by the patient's native chordae tendineae 57. The artificial chordae tendineae 33, 36 are omitted from FIGS. 4 and 5 for clarity. In FIG. 4, the inflated balloon 20 is in its proximal position between atrioventricular leaflets 55 which separate the ventricle 50 from the atria 60. In the position shown in FIG. 4, the proximal end of balloon 20 is just distal of the patient's tricuspid annulus. FIG. 5 illustrates an example of the position of balloon 20 during the diastolic phase during which the balloon 20 moves distally to allow ventricular filling without obstructing the inflow of blood into the ventricle or creating a stenosis.

It will be appreciated that different patients, whether human or other mammals such as dogs, have different size hearts. In order to obtain the proper positioning of the inflated balloon, proper sealing and other functionality such as not creating undue obstruction to blood flow, when using the embodiment shown in FIGS. 1-6 and 8, it is necessary to use different sized valve devices, for example having shafts of different lengths and different size balloons.

According to other embodiments, the points of attachment of the artificial chordae tendineae to the guide shaft are adjustable. This allows a surgeon to change and fine tune the range of motion of the balloon relative to the guide shaft in situ after or before the guide shaft has been anchored in place. Of course, the adjustment can also be made outside of the patient's body.

Figure 6:
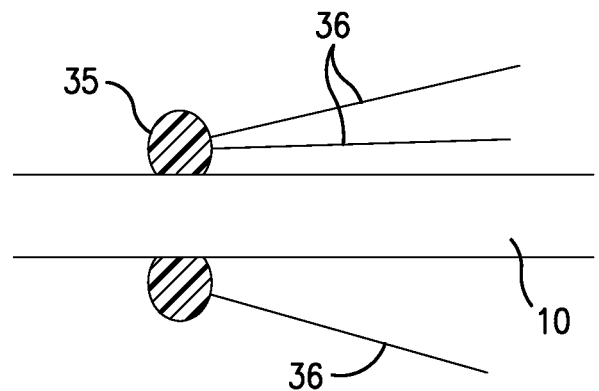
FIG. 6 is a partial, cross-sectional view of a range limiting structure of the present invention.

With reference to FIG. 6 which is a partial view of a further embodiment, the artificial chordae tendineae 36 are fixed to a ring 35 which has a selectively adjustable fit with guide shaft 10 which prevents movement relative to shaft 10 under conditions normally encountered in a heart, but can be repositioned with suitable surgical instruments. In other words, ring 35 is sized to fit very snuggly on shaft 10 and will not normally move relative to shaft 10 during the cardiac cycle, but can be purposely repositioned by a surgeon during surgery to adjust the range of movement of the balloon relative to the shaft.

Figure 7:
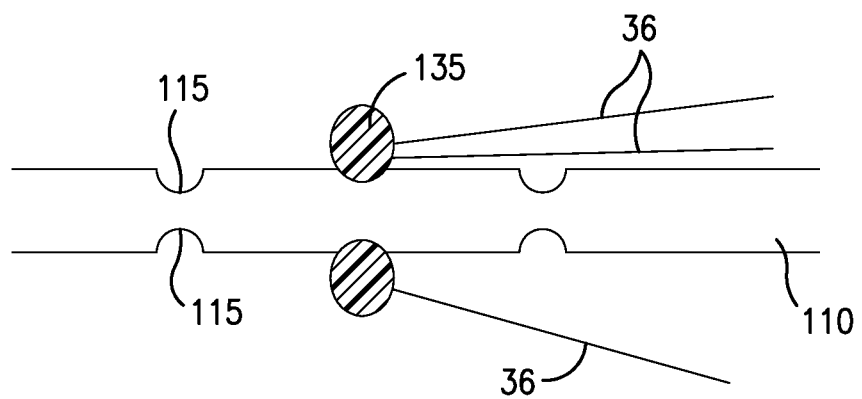
FIG. 7 is a partial, cross-sectional view of an alternative range limiting structure of the present invention.

FIG. 7 illustrates a still further embodiment wherein guide shaft 110 is provided with a plurality of grooves 115 which partially receive a ring 135. In this embodiment, the artificial chordae tendineae 36 are fixed to ring 135, and ring 135 is sized to fit very snuggly within grooves 115 on shaft 110 and will not move relative to shaft 10 except when ring 135 is purposely repositioned by a surgeon during surgery.

While rings 35 and 135 and guide shaft 110 have been described and illustrated with the distal artificial chordae tendineae, similar proximal rings 35' and 135' are provided when desired for adjustably connecting the proximal artificial chordae tendineae to the guide shaft. Rings 35, 135 can be formed of suitable biocompatible polymeric or rubber-like materials.

Figure 8:
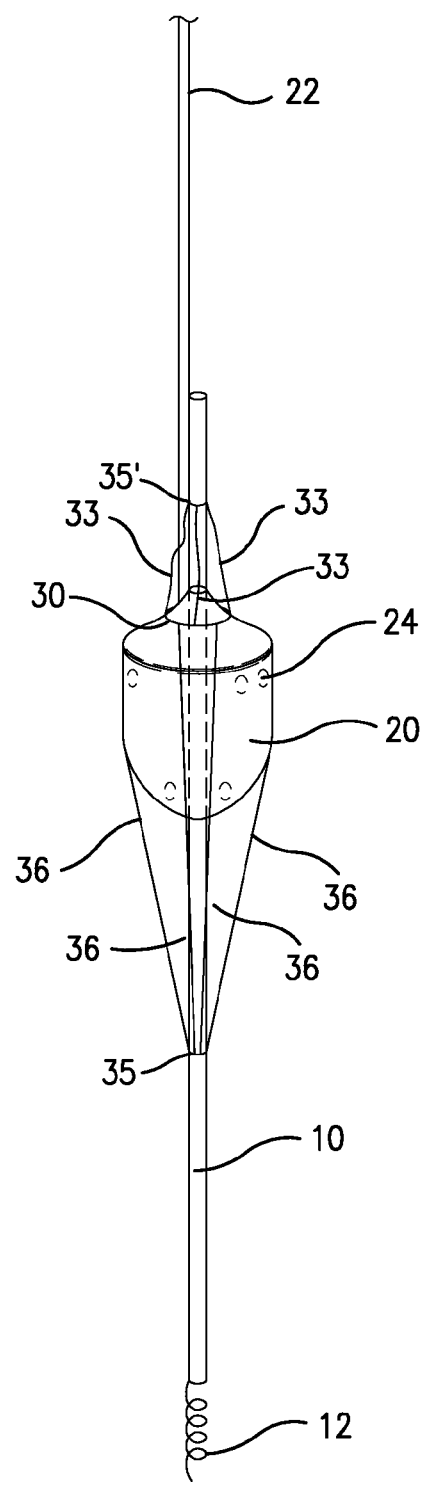
FIG. 8 is a perspective view of the valve device of FIG. 1.
Figure 9:
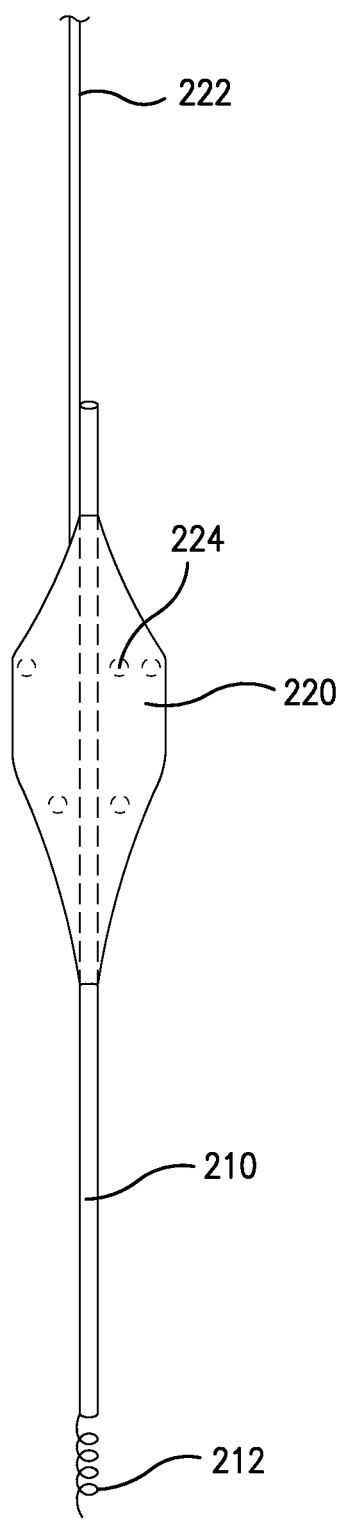
FIG. 9 is a partial view of a valve device of a second embodiment of the present invention.
Figure 12:
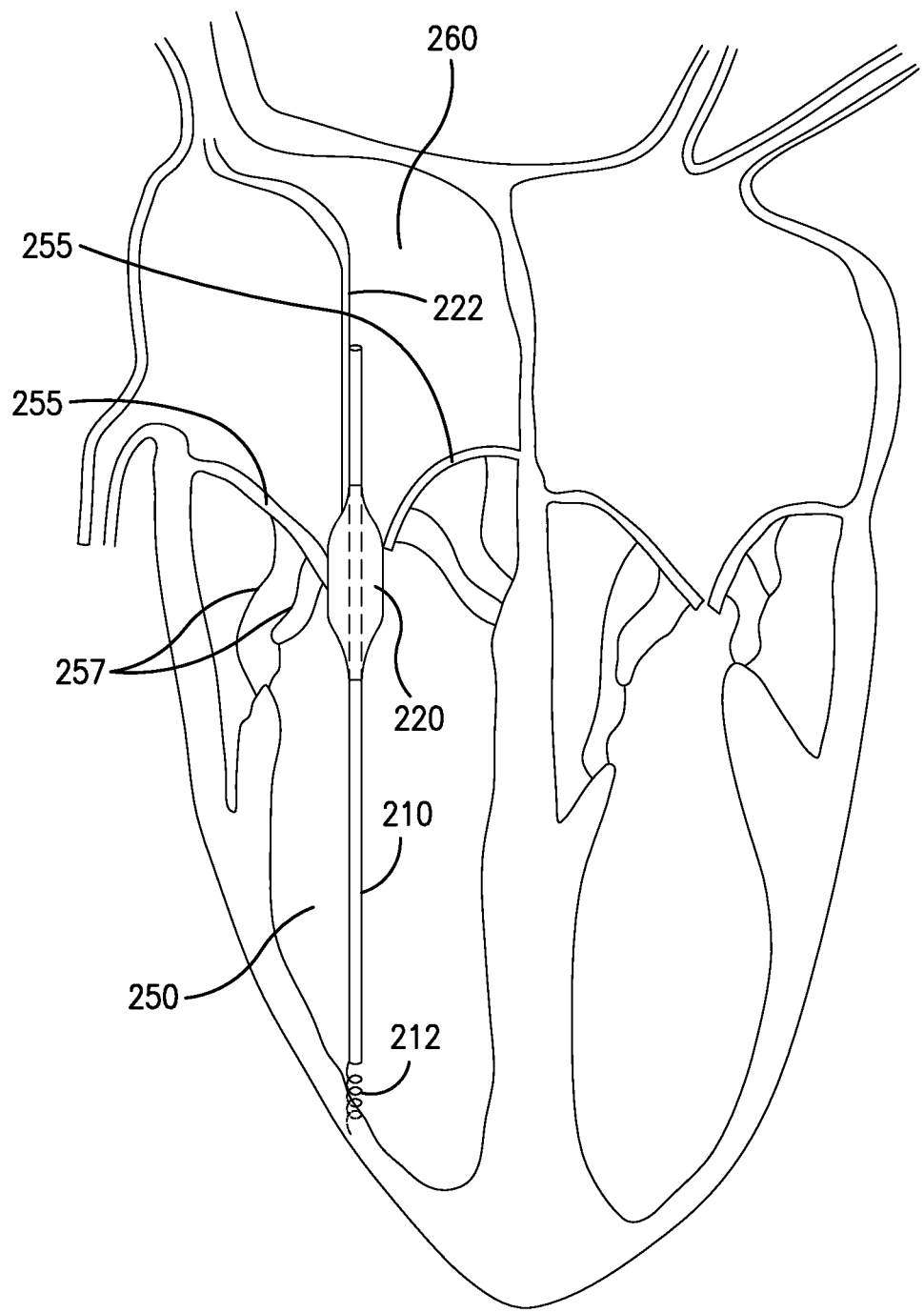
FIG. 12 is a view of a valve device of FIG. 9 shown in a heart during the systolic portion of the heart cycle.
Figure 13:
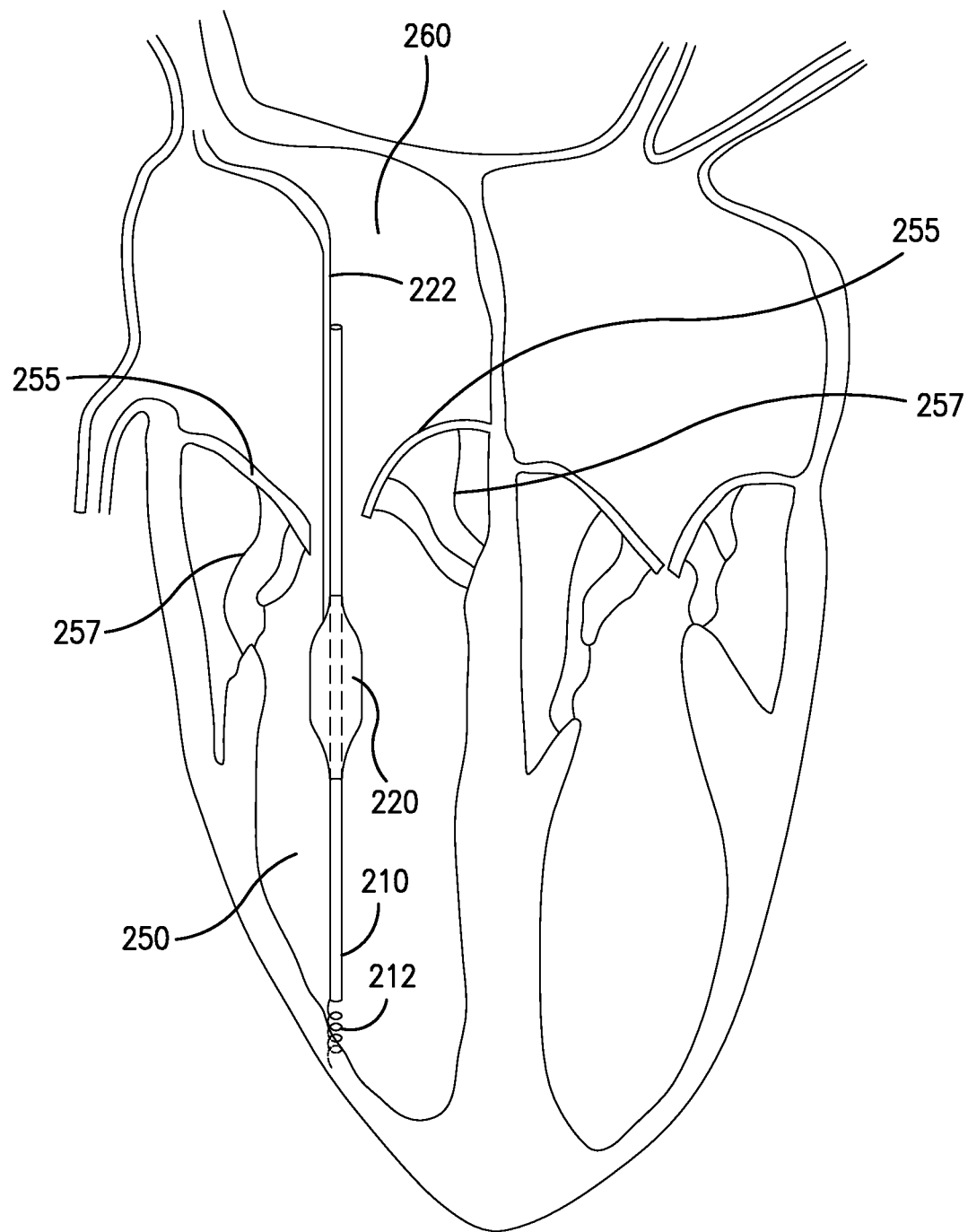
FIG. 13 is a view of a valve device of FIG. 9 shown in a heart during the diastolic portion of the heart cycle.
Figure 14:
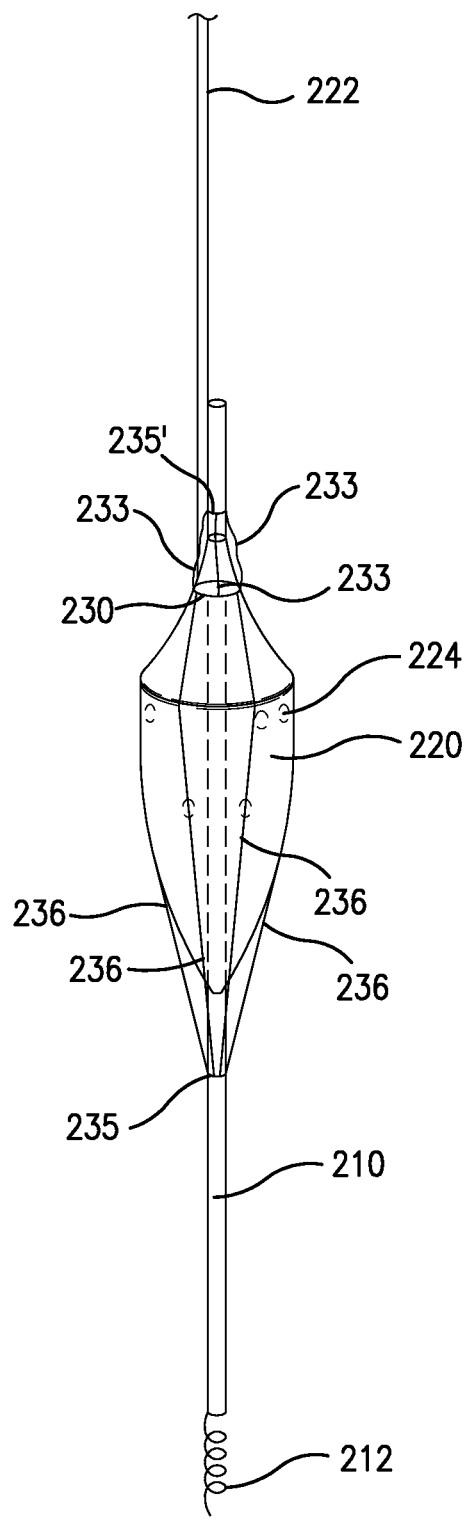
FIG. 14 is a perspective view of the valve device of FIG. 9.

FIG. 8 is a perspective view of the heart valve implant shown in FIGS. 2 and 3.

FIGS. 9-14 correspond to the views shown in FIGS. 1-5 and 8 and illustrate a preferred embodiment of the present invention wherein the heart valve implant comprises an inflatable valve body with more tapered proximal and distal ends. The heart valve implant of this embodiment comprises a guide shaft 210, anchor 212, inflatable valve body 220 comprising markers 224, inflation lumen 222, proximal artificial chordae tendinae 233 connected to pseudo annulus ring 230 and distal artificial chordae tendinae 236. This embodiment is deployed in the same manner as the embodiment shown in FIGS. 1-6 and 8.

During surgery, the valve comprising a deflated balloon is inserted through a delivery device, such as a guiding catheter, and the distal end of the valve device is fixed, preferably into the apex of the related ventricle via active fixation corkscrew mechanism 12. Once the device is fixed in position, the occluder balloon 20 is inflated via inflation lumen 22 with a mixture of saline and iodinated contrast material or an injectable polymer. The valve device is observed by the surgeon via fluoroscopy and positioned so that balloon 20 sits between the leaflets of the native atrioventricular valve leaflets during the systolic portion of the cardiac cycle. This positioning of the valve occludes blood from regurgitating back into the atria. At the beginning of the diastolic portion of the cardiac cycle the balloon moves into the ventricle allowing for ventricular filling without creating a stenosis or obstruction to inflow. According to certain methods, the surgeon also performs the step of moving one or more of the attachment rings 35, 35' relative to the guide shaft in order to adjust the range of movement of the inflatable valve body relative to the guide shaft. The entire guide shaft and/or the inflation lumen, including the injection port for the inflation lumen, can remain attached to the patient or can be detached at some desired point proximal to the attachment site, e.g. attachment ring 35', of the proximal artificial chordae tendineae.

The embodiments of the present invention offer several significant advantages. Since they are balloon based, they have a low profile. If desired, the illustrated embodiments can be inserted through narrow blood vessels via a transcatheter venous approach with an 8 French catheter. Many other devices require 18-24 French delivery catheters which can significantly limit vascular access. The sealing function of the presently described devices relies, in part, on the native structure of the atrioventricular valve so this native structure of the patient's heart is not required to be removed for deployment of the disclosed devices. This reduces the time of surgery and discomfort to the patient. The present valves also rely upon the use of less hardware in the heart when compared to some previously known artificial valves. The movability of the balloon relative to the guide shaft advantageously minimizes the obstruction to blood flow. The preferred tapered configuration of the proximal and distal portions of the inflatable valve body promotes laminar blood flow around the balloon thereby decreasing the likelihood of thrombogenesis. The adjustability of the attachment sites between the artificial chordae tendineae and the guide shaft allows for adjustments to the range of movement of the balloon relative to the guide shaft to be made during deployment to maximize the reduction of the regurgitant jet. The device is deployed via a transcatheter venous method and as a result is much less invasive than traditional open heart surgery and does not require cardiopulmonary bypass. Unlike many known heart valve implants, embodiments of the present invention are retrievable from the patient.

The invention claimed is:

1. A heart valve implant comprising:
    a guide shaft comprising a first end and a second end;
    an anchor coupled to said guide shaft proximate said first end;
    an inflatable valve body movably connected to said guide shaft within a predetermined range of movement, said inflatable valve body comprising an outer diameter;
    range limiting structure which limits the range of movement of said inflatable valve body relative to said guide shaft comprising:
    a pseudo-annulus ring having an internal diameter which is smaller than said outer diameter of said inflatable valve body,
    a plurality of proximal artificial chordae tendineae which are connected to said guide shaft and to said pseudo-annulus ring for limiting the movement of said pseudo-annulus ring in a distal direction, and
    a plurality of distal artificial chordae tendineae which are connected to said guide shaft and said pseudo-annulus ring for limiting the movement of said pseudo-annulus ring in a proximal direction.

2. A heart valve implant according to claim 1 wherein said range limiting structure is selectively repositionable relative to said guide shaft.

3. A heart valve implant according to claim 1 wherein said range limiting structure is configured for in situ adjustment of said artificial chordae tendineae relative to said guide shaft in order to adjust the range of movement of said inflatable valve body relative to said guide shaft.

4. A heart valve implant according to claim 3 wherein said inflatable valve body is slidably mounted on said guide shaft.

5. A heart valve implant according to claim 1 wherein said inflatable valve body is slidably mounted on said guide shaft.

6. A heart valve implant according to claim 1 wherein said at least one of said proximal artificial chordae tendineae or said distal artificial chordae tendineae are connected to an attachment ring which is attached to said guide shaft.

7. A heart valve implant according to claim 6 wherein attachment ring is selectively movable relative to said guide shaft.

8. A heart valve implant according to claim 6 wherein said guide shaft comprises at least one recess adapted to receive said attachment ring.

9. A heart valve implant according to claim 1 wherein said inflatable valve body comprises discernible metal markers which can be detected radiographically during surgery.

10. A heart valve implant according to claim 1 wherein said pseudo-annulus ring is collapsible.

11. A heart valve implant according to claim 1 wherein said pseudo-annulus ring is flexible.

12. A heart valve implant according to claim 11 wherein said artificial chordae tendineae are formed of a flexible, ePTFE suture material.

13. A heart valve implant according to claim 1 wherein said pseudo-annulus ring is formed of a flexible, ePTFE suture material.

14. A heart valve implant according to claim 1 wherein said artificial chordae tendineae are formed of a flexible, ePTFE suture material.

15. A heart valve implant comprising:
    a guide shaft comprising a first end and a second end;
    an anchor coupled to said guide shaft proximate said first end;
    an inflatable valve body slidably connected to said guide shaft within a predetermined range of movement, said inflatable valve body comprising an outer dimension; and
    range limiting structure for limiting the range of movement of said inflatable valve body relative to said guide shaft, said range limiting structure comprising:

a pseudo-annulus ring comprising an internal dimension which is less than the outer dimension of said inflatable valve body;

a plurality of proximal flexible filaments connected to said pseudo-annulus ring and said guide shaft which limit the range of movement of said inflatable valve body relative to said guide shaft in a distal direction, and a plurality of distal flexible filaments connected to said pseudo-annulus ring and said guide shaft which limit the range of movement of said inflatable valve body relative to said guide shaft in a proximal direction.

16. A heart valve implant according to claim 15 wherein said filaments comprise ePTFE.

17. A heart valve implant according to claim 15 wherein said flexible filaments are selectively, movably connected to said guide shaft.

18. A heart valve implant according to claim 15 wherein said range of movement is adjustable.

19. A heart valve implant according to claim 15 wherein said inflatable valve body is slidably mounted on said guide shaft.

20. A heart valve implant according to claim 15 further comprising at least one attachment ring connected to said flexible filaments and selectively, adjustable with respect to said guide shaft.

21. A heart valve implant according to claim 15 wherein said inflatable valve body is tapered on at least one end.

22. A heart valve implant according to claim 21 wherein said inflatable valve body is tapered on both ends.

23. A method of deploying a heart valve implant in a patient comprising the steps of:

providing a heart valve implant comprising:

a guide shaft comprising a first end and a second end;

an anchor coupled to said guide shaft proximate said first end;

an inflatable valve body slidably connected to said guide shaft within a predetermined range of movement, said inflatable valve body comprising an outer dimension;

at least one range limiting structure which limits the range of movement of said inflatable valve body relative to said guide shaft, said range limiting structure comprising:

a pseudo-annulus ring having an internal diameter which is smaller than said outer diameter of said inflatable valve body, a plurality of proximal artificial chordae tendineae which are connected to said guide shaft and to said pseudo-annulus ring for limiting the movement of said pseudo-annulus ring in a distal direction, and a plurality of distal artificial chordae tendineae which are connected to said guide shaft and said pseudo-annulus ring for limiting the movement of said pseudo-annulus ring in a proximal direction;

positioning said heart valve implant at least partially within a heart via a transcatheter venous procedure;

securing said anchor to native heart tissue; and adjusting the range of movement of said inflatable valve body relative to said guide shaft.

24. A method of deploying a heart valve implant in a patient according to claim 23 wherein said adjusting step comprises changing the position of said range limiting structure relative to said guide shaft.

* * * * *